(12) United States Patent
Liu et al.

(10) Patent No.: US 8,236,860 B2
(45) Date of Patent: Aug. 7, 2012

(54) **INHIBITION OF THE SURVIVAL OF PANCREATIC CANCER BY CYCLOHEXENONE COMPOUNDS FROM *ANTRODIA CAMPHORATA***

(75) Inventors: Sheng-Yun Liu, Taipei Hsien (TW); Wu-Che Wen, Taipei Hsien (TW); Mao-Tien Kuo, Taipei Hsien (TW)

(73) Assignee: Golden Biotechnology Corporation, Taipei Hsien (TW)

( * ) Notice: Subject to any disclaimer, the term of this patent is extended or adjusted under 35 U.S.C. 154(b) by 0 days.

(21) Appl. No.: 12/832,548

(22) Filed: Jul. 8, 2010

(65) Prior Publication Data

US 2011/0009494 A1    Jan. 13, 2011

(30) Foreign Application Priority Data

Jul. 9, 2009   (TW) ............................... 98123264 A

(51) Int. Cl.
*C07C 49/543* (2006.01)
*C07C 49/557* (2006.01)
*A61K 31/12* (2006.01)

(52) U.S. Cl. ........................................ 514/690; 568/377

(58) Field of Classification Search .................. 514/690; 568/377
See application file for complete search history.

(56) References Cited

U.S. PATENT DOCUMENTS

| | | | |
|---|---|---|---|
| 7,342,137 B1 * | 3/2008 | Liu et al. ........................ | 568/377 |
| 2011/0059122 A1 * | 3/2011 | Liu et al. .................. | 424/195.15 |
| 2011/0059123 A1 * | 3/2011 | Liu et al. .................. | 424/195.15 |
| 2011/0060055 A1 * | 3/2011 | Liu et al. ........................ | 514/690 |
| 2011/0060056 A1 * | 3/2011 | Liu et al. ........................ | 514/690 |
| 2011/0060057 A1 * | 3/2011 | Liu et al. ........................ | 514/690 |
| 2011/0060058 A1 * | 3/2011 | Liu et al. ........................ | 514/690 |

OTHER PUBLICATIONS

I-Hwa Cherng et al., Three New Triterpenoids from Antrodia Cinnamomea, Journal of Natural Products, Mar. 1995, pp. 365-371, vol. 58, No. 3.

Chung-Hsiung Chen et al., New Steroid Acids from Antrodia Cinnamomea, a Fungal Parasite of Cinnamomum Micranthum, Journal of Natural Products, Nov. 1995, pp. 1655-1661, vol. 58, No. 11.

Hung-Chen Chiang et al., A Sesquiterpene Lactone, Phenyl and Biphenyl Compounds from Antrodia Cinnamomea, Phytochemistry, 1995, pp. 613-616, vol. 39, No. 3, Great Britain.

I-Hwa Cherng et al., Triterpenoids from Antrodia Cinnamomea, Phytochemistry, 1996, pp. 263-267, vol. 41, No. 1, Great Britain.

Shu-Wei Yang et al., Steroids and Triterpenoids of Antrodia Cinnamomea—a Fungus Parasitic on Cinnamomum Micranthum, Phytochemistry, 1996, pp. 1389-1392, vol. 41, No. 5, Great Britain.

* cited by examiner

*Primary Examiner* — Brandon Fetterolf
*Assistant Examiner* — Anna Pagonakis
(74) *Attorney, Agent, or Firm* — Muncy, Geissler, Olds & Lowe, PLLC

(57) ABSTRACT

The present invention relates to a novel application of a compound. The compound 4--2,3-dimethoxy-6-methyl-5-(3,7,11-trimethyl-dodeca-2,6,10-trienyl)-cyclohex-2-enone of the invention is isolated and purified from the extracts of *Antrodia camphorata*, which can be applied for inhibiting the survival of pancreatic cancer cells and be used as a pharmaceutical composition to inhibit the pancreatic tumor growth.

19 Claims, No Drawings

INHIBITION OF THE SURVIVAL OF PANCREATIC CANCER BY CYCLOHEXENONE COMPOUNDS FROM ANTRODIA CAMPHORATA

BACKGROUND OF THE INVENTION

1. Field of the Invention

The present invention relates to a new application for inhibiting cancer cell survival, in particular to the application for inhibiting the survival of pancreatic cancer cells by a compound isolated and purified from *Antrodia camphorata*.

2. The Prior Arts

Pancreatic cancer is the fourth leading cause of cancer death in Western countries and is also the tenth leading cause of cancer death in Taiwan. Approximately 60 percent of pancreatic cancer arises in the head of pancreas, and about 21 percent invades to whole pancreas. Pancreatic ductal adenocarcinoma, the most common cancer of exocrine pancreatic tumors, accounts for 85~90 percent for all types of pancreatic cancer.

Pancreatic cancer is an aggressive and highly mortal malignancy. Conventional therapy for the cancer includes surgery, chemotherapy and radiation, wherein the curative effect of surgery is better among them. However, only 15~20 percent of patients have the opportunity to receive surgical resection and the overall 5-year survival rate of surgically operated patients is less than 20 percent. Although patients need to have radiation therapy administered usually with chemotherapy when tumor size is too large to be completely excised by surgery to raise cure rate, it isn't beneficial in total survival rate. In addition, the prognosis for pancreatic cancer is very poor because pancreatic cancer is located in the upper abdomen in the retroperitoneum and is unable to be found in early stage. The symptoms will not appear until the tumor grows to an unmanaged size. Therefore, metastasis is diagnosed in two third of pancreatic cancer patients at the initial diagnosis.

The diagnosis and confirmation of partially invasive or unresectable pancreatic cancer is usually late and cannot be cured by surgery. Also the treatment effects achieved by traditional chemotherapy drugs and radiation are limited. Furthermore, the side effects to human body caused by chemotherapy drugs should not be underestimated. Therefore, it is urgently needed to develop an effective therapeutic substance with mild side effects for applying to the clinical therapy of pancreatic cancer.

*Antrodia camphorata* is also known as various names such as Chang-Chih, *Ganoderma comphoratum, Antrodia camphorata, Taiwanofungus camphorata*, and Camphor Mushroom . . . etc., a genus of *Basidiomycoya, Homobasidiomycetes, Aphyllophorales, Polyporaceae*, and *Antrodia* in Fungi, and also a perennial mushroom. It is a Taiwan endemic species of fungi and received its name because it only grows on the inner wall of the hollow material from Taiwan's endemic *Lauraceae* tree species, *Cinnamomum kanehirai*. The price of *Antrodia camphorata* is very high due to the extremely slow growth rate of natural *Antrodia camphorata*.

The fruiting bodies of *Antrodia camphorata* are perennial, sessile, hard and woody, which exhale strong smell of sassafras (camphor aroma). The appearances are various with plate-like, bell-like, hoof-like, or tower-like shapes. They are reddish in color and flat when young, attached to the surface of wood. Then the brims of the front end become reversely curled tilting and extending to the surroundings. At the same time, the color turns to be faded red-brown or cream yellow brown, with ostioles all over. This region is of very high medical value.

In traditional Taiwanese medicine, the curative effects of *Antrodia camphorata* include removing rheumatism, smoothing vitality, nourishing blood, eliminating bruises, benefiting spleen and stomach, lessening accumulation, detoxification, subsiding swelling, sedation and relieving pain, and is used as a great antidote for detoxifying food poisoning, diarrhea, vomiting and pesticide poisoning. Furthermore, it has adjuvant therapeutic effects on liver and stomach dysfunction and the diseases of blood circulation. *Antrodia camphorata*, like general edible and medicinal mushrooms, is rich in numerous nutrients including polysaccharides (such as β-glucosan), triterpenoids, superoxide dismutase (SOD), adenosine, proteins (immunoglobulins), vitamins (such as vitamin B, nicotinic acid), trace elements (such as calcium, phosphorus and germanium and so on), nucleic acid, agglutinin, amino acids, steroids, lignins and stabilizers for blood pressure (such as antrodia acid) and so on. These physiologically active ingredients are believed to exhibit effects such as: anti-tumor activities, increasing immunomodulating activities, anti-allergy, anti-bacteria, anti-hypertension, decreasing blood sugar, decreasing cholesterol, etc.

Triterpenoids are the most studied components among the numerous compositions of *Antrodia camphorata*. Triterpenoids are the summary terms for natural compounds, which contain 30 carbon atoms with the pent- or hex-acyclic structures. The bitter taste of *Antrodia camphorata* is from the component of triterpenoids. Three novel ergostane-type triterpenoids (antcin A, antcin B, antcin C) were isolated by Cherng et al. from the fruiting bodies of *Antrodia camphorata* (Cherng, I. H., and Chiang, H. C. 1995. Three new triterpenoids from *Antrodia cinnamomea*. J. Nat. Prod. 58:365-371). Three new compounds zhankuic acid A, zhankuic acid B and zhankuic acid were extracted from the fruiting bodies of *Antrodia camphorata* with ethanol by Chen et al. (Chen, C. H., and Yang, S. W. 1995. New steroid acids from *Antrodia cinnamomea*,—a fungus parasitic on *Cinnamomum micranthum*. J. Nat. Prod. 58:1655-1661). In addition, Cherng et al. also found three other new triterpenoids from the fruiting bodies of *Antrodia camphorata*, which are sesquiterpene lactone and 2 biphenyl derived compounds, 4,7-dimethoxy-5-methyl-1,3-benzodioxole and 2,2',5,5'-teramethoxy-3,4,3', 4'-bi-methylenedioxy-6,6'-dimethylbiphenyl (Chiang, H. C., Wu, D. P., Cherng, I. W., and Ueng, C. H. 1995. A sesquiterpene lactone, phenyl and biphenyl compounds from *Antrodia cinnamomea*. Phytochemistry. 39:613-616). In 1996, four novel ergostane-type triterpenoids (antcins E and F and methyl antcinates G and H) were isolated by Cherng et al. with the same analytic methods (Cherng, I. H., Wu, D. P., and Chiang, H. C. 1996. Triteroenoids from *Antrodia cinnamomea*. Phytochemistry. 41:263-267). And two ergostane related steroids, zhankuic acids D and E together with three lanosta related triterpenes, 15 alpha-acetyl-dehydrosulphurenic acid, dehydroeburicoic acid, and dehydrosulphurenic acid were isolated by Yang et al. (Yang, S. W., Shen, Y. C., and Chen, C. H.1996. Steroids and triterpenoids of *Antrodia cinnamomea*—a fungus parasitic on *Cinnamomum micranthum*. Phytochemistry. 41:1389-1392).

Although *Antrodia camphorata* extracts were reported to have the above mentioned effects from the previously published experimental results, and the several compounds were analyzed and identified successfully, further works are needed to identify the effective compounds to inhibit cancer growth and thus to contribute beneficial effects on cancer therapy such as the treatment and prevention of pancreatic cancer.

SUMMARY OF THE INVENTION

In order to identify the anti-cancer compounds from the extracts of *Antrodia camphorata*, the compound of the formula (1) was isolated and purified in the present invention,

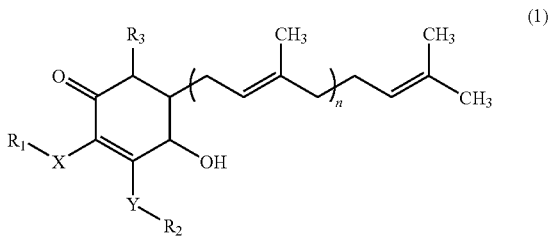

(1)

wherein X and Y can be oxygen, nitrogen or sulfur, $R_1$, $R_2$ and $R_3$ are each a hydrogen atom, methyl or $(CH_2)_m$—$CH_3$ and m=1–12; n=1–12.

A preferred compound of the general formula (1) is 4--2,3-dimethoxy-6-methyl-5-(3,7,11-trimethyl-dodeca-2,6,10-trienyl)-cyclohex-2-enone as shown in formula (2), with molecular formula of $C_{24}H_{38}O_4$, appearance of pale yellow powder and molecular weight of 390.

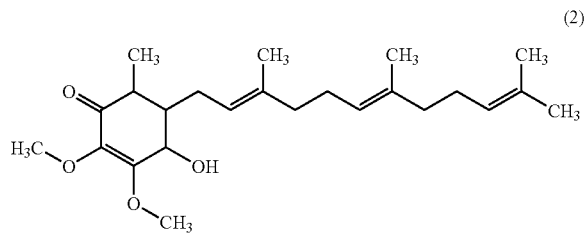

(2)

Cyclohexenone compounds having the structures of formula (1) and formula (2) are purified from aqueous extraction or organic solvent extraction of *Antrodia camphorata*. The organic solvents used include, but not limited to, alcohols such as methanol, ethanol or propanol, esters such as ethyl acetate, alkanes such as hexane, or halogenated alkanes such as chloromethane, chloroethane. Among them, alcohol is preferred, and ethanol is particularly preferred.

Cyclohexenone compounds of the present invention are applied in inhibiting the survival of cancer cells, which can further be used as a pharmaceutical composition for treating cancer and to enhance the cancer therapeutic effects. The compounds of the invention can be applied in inhibiting the survival of pancreatic cancer cells, which result in delaying the growth of the cancer cells and suppressing proliferation of the cancer cells, and further inhibiting cancer deterioration. The preferred compound is 4--2,3-dimethoxy-6-methyl-5-(3,7,11-trimethyl-dodeca-2,6,10-trienyl)-cyclohex-2-enone of the formula (2).

On the other hand, the compounds of formula (1) and/or formula (2) in the present invention can be incorporated into pharmaceutical compositions for treating pancreatic cancer to inhibit the survival of cancer cells. The pharmaceutical compositions include not only the compounds of formula (1) and/or formula (2), but also the pharmaceutically accepted carriers. Examples of such carriers include, but are not limited to, excipients such as water, fillers such as sucrose or starch, binders such as cellulose derivatives, diluents, disintegrants, absorption enhancers or sweeteners. The pharmaceutical composition can be manufactured through mixing the compounds of formula (1) and/or formula (2) with at least one of the carriers by means of conventional methods known in the pharmaceutically technical field, which can be formulated in the form of, but are not limited to, powder, tablets, capsules, pellets, granules or other liquid formulation.

The present invention is further explained in the following embodiment illustration and examples. Those examples below should not, however, be considered to limit the scope of the invention, it is contemplated that modifications will readily occur to those skilled in the art, which modifications will be within the spirit of the invention and the scope of the appended claims.

DETAILED DESCRIPTION OF THE PREFERRED EMBODIMENT

The aqueous or organic solvent extracts of *Antrodia camphorata* were subjected to high-performance liquid chromatography (HPLC) for isolation and purification. Each fraction was recovered and applied to anti-cancer assay. The potent fractions with anti-cancer effects were analyzed for the composition and further assayed against pancreatic cancer cells. The above approach then led to the identification of compounds of formula (1) and formula (2) in inhibiting the survival of pancreatic cancer cells.

The compound 4--2,3-dimethoxy-6-methyl-5-(3,7,11-trimethyl-dodeca-2,6,10-trienyl)-cyclohex-2-enone of the formula (2) is explained below as an example for the present invention. The anti-cancer effects of 4--2,3-dimethoxy-6-methyl-5-(3,7,11-trimethyl-dodeca-2,6,10-trienyl)-cyclohex-2-enone was assessed using 3-(4,5-dimethylthiazol-2-yl)-2,5-diphenyltetrazolium bromide MTT) assay according to the anti-cancer drug screening model of National Cancer Institute (NCI) to analyze survival rates on pancreatic cancer cell line BxPC-3. These assays have proved that cyclohexenone compounds from *Antrodia camphorata* decreased the survival rates of pancreatic cancer cell line BxPC-3, and simultaneously showed low half inhibition concentration ($IC_{50}$) value. Therefore, cyclohexenone compounds from *Antrodia camphorata* can be used for inhibiting the survival of pancreatic cancer cells and further be applied for the treatment of pancreatic cancer. The details of the examples are described as follows:

EXAMPLE 1

Isolation of 4--2,3-dimethoxy-6-methyl-5-(3,7,11-trimethyl-dodeca-2,6,10-trienyl)-cyclohex-2-enone One hundred grams of mycelia, fruiting bodies or mixture of both from *Antrodia camphorata* were placed into a flask. A proper amount of water and alcohol (70-100% ethanol solution) was added into the flask and were stirred at 20-25° C. for at least 1 hour. The solution was filtered through both a filter paper and a 0.45 μm membrane, and then collected as the extract.

The extract of *Antrodia camphorata* was subjected to High Performance Liquid chromatography (HPLC) analysis. The separation was performed on a RP18 column using a mobile phase consisted of methanol (A) and 0.1-0.5% acetic acid (B), with the gradient conditions: the ratio of (B) from 95% to 20% 0-10 minutes, from 20% to 10% 10-20 minutes, kept 10% 20-35 minutes, and increased from 10% to 95% 35-40 minutes at the flow rate of 1 ml/min. The column effluent was monitored with a UV-visible detector.

The fractions collected during 25-30 min were concentrated to yield 4--2,3-dimethoxy-6-methyl-5-(3,7,11-trimethyl-dodeca-2,6,10-trienyl)-cyclohex-2-enone, a product of pale yellow powder. The analysis of 4--2,3-dimethoxy-6-methyl-5-(3,7,11-trimethyl-dodeca-2,6,10-trienyl)-cyclohex-2-enone showed the molecular formula of $C_{24}H_{38}O_4$, molecular weight of 390, and melting point of 48° C.~52° C. Investigation of NMR spectra showed that $^1$H-NMR (CDCl$_3$) δ(ppm)=1.51, 1.67, 1.71, 1.75, 1.94, 2.03, 2.07, 2.22, 2.25, 3.68, 4.05, 5.07, and 5.14; $^{13}$C-NMR(CDCl$_3$)δ(ppm)=12.31, 16.1, 16.12, 17.67, 25.67, 26.44, 26.74, 27.00, 39.71, 39.81, 4.027, 43.34, 59.22, 60.59, 120.97, 123.84, 124.30, 131.32, 135.35, 135.92, 138.05, 160.45, and 197.12.

EXAMPLE 2

In Vitro Survival Assay for Anti-Pancreatic Cancer Effects

Inhibiting effects of pancreatic cancer cells by cyclohexenone compounds of *Antrodia camphorata* from example 1 were assessed according to the anticancer-drug screening model of National Cancer Institute (NCI). The compound 4--2,3-dimethoxy-6-methyl-5-(3,7,11-trimethyl-dodeca-2,6,10-trienyl)-cyclohex-2-enone from example 1 was added into the culture media of pancreatic cancer cell line BxPC-3 to determine the survival rates. Survival of cell was analyzed using MTT assay. BxPC-3 cell line was a ductal adenocarcinoma cell line.

MTT assay is commonly used to analyze cell proliferation, survival rate of viable cells and cytotoxicity. MTT (3[4,5-dimethylthiazol-2-yl]-2,5-diphenyltetrazolium bromide) is a yellow dye which can be converted to water-insoluble purple formazan on the reductive cleavage of its tetrazolium ring by the succinate tetrazolium reductase in mitochondria of cells. The amount of formazan produced is used to detect the number of viable cells and calculate the survival rates.

The BxPC-3 cells were cultivated in RPMI 1640 medium supplemented with 10% fetal bovine serum, 100 IU/ml of Penicillin and 100 mg/ml of Streptomycin at 37° C., 5% $CO_2$ for 24 hours. Proliferated cells were washed once with PBS, treated with 1× tryspin-EDTA, and centrifuged at 1200 rpm for 5 min. The supernatant was removed and the cell pellet was resuspended in 10 ml of fresh medium by gently shaking. Cells were seeded onto 96-well plates. Cells treated with the crude extracts of *Antrodia camphorata* (total ethanol extracts, not purified) were designed as the control group; and cells treated with 4--2,3-dimethoxy-6-methyl-5-(3,7,11-trimethyl-dodeca-2,6,10-trienyl)-cyclohex-2-enone were designed as the experiment group. Both substrates were added in the concentration of 30, 10, 3, 1, 0.3, 0.1 and 0.03 μg/ml respectively. Cells were cultivated at 37° C., 5% $CO_2$ for 48 hours. Afterward, 2.5 mg/ml of MIT solution was added to each well and incubated in the dark for 4 hours, followed by the addition of 100 μl of lysis buffer to stop the reaction. The absorbances were measured at 570 nm with an ELISA Reader to determine the survival rates. The half inhibition concentration (IC$_{50}$) value was also calculated and listed in Table 1.

TABLE 1

Results of in vitro survival assay for inhibition of pancreatic cancer cells

| Sample | IC$_{50}$ (μg/ml) |
| --- | --- |
| Experiment group (formula 2) BxPC-3 | 1.44 |

Refers to the result of table 1, the IC$_{50}$ value of 4--2,3-dimethoxy-6-methyl-5-(3,7,11-trimethyl-dodeca-2,6,10-trienyl)-cyclohex-2-enone toward BxPC-3 was 1.44 μg/ml, which was significantly lower than those of total extracts from *Antrodia camphorata* (data not shown). Therefore, 4--2,3-dimethoxy-6-methyl-5-(3,7,11-trimethyl-dodeca-2,6,10-trienyl)-cyclohex-2-enone from *Antrodia camphorata* can be utilized to inhibit the survival of pancreatic cancer cells.

In summary, the compound 4--2,3-dimethoxy-6-methyl-5 (3,7,11-trimethyl-dodeca-2,6,10-trienyl)-cyclohex-2-enone isolated from Antrodia camphorata according to the present invention can be used to effectively inhibit the survival of human pancreatic cancer cells. The cyclohexenone compounds from *Antrodia camphorata* won't induce uncomfortable side effects, toxicity or complications when being applied for treating pancreatic cancer. Moreover, these compounds of the invention can also be used concurrently with chemotherapy drugs when treating pancreatic cancer in order to reduce the using amount of chemotherapy drugs as well as decreasing the side effects resulted from chemotherapy drugs. In addition, it can be incorporated into pharmaceutical compositions. The pharmaceutical compositions include not only effective amount (or active dose) of the cyclohexenone compounds from *Antrodia camphorata* of the present invention, but also the pharmaceutically accepted carriers. Examples of such carriers include, but are not limited to, excipients such as water, fillers such as sucrose or starch, binders such as cellulose derivatives, diluents, disintegrants, absorption enhancers or sweeteners. The composition of the present invention can be manufactured through mixing the compound of cyclohexenone from *Antrodia camphorata* with at least one of the carriers by means of conventional methods known in the pharmaceutically technical field, and can be formulated in the forms of powder, tablets, capsules, pellets, granules or other liquid formulation, but are not limited to. The purpose for treating pancreatic cancer can then be accomplished.

What is claimed is:

1. A method of inhibiting the survival of pancreatic cancer cells, comprising administering to a subject in need thereof an effective amount of a compound having the following formula:

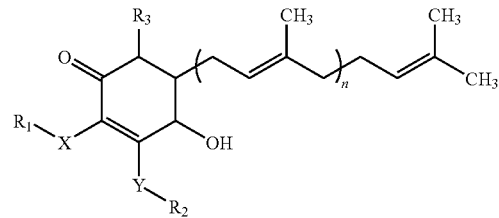

wherein X and Y is oxygen, nitrogen or sulfur, $R_1$, $R_2$ and $R_3$ are each a hydrogen atom, methyl or $(CH_2)_m$—$CH_3$, and m=1-12; n=1-12.

2. The method as claimed in claim 1, wherein the compound is 4--2,3-dimethoxy-6-methyl-5-(3,7,11-trimethyl-dodeca-2,6,10-trienyl)-cyclohex-2-enone.

3. The method as claimed in claim 2, wherein the compound is isolated from *Antrodia camphorata*.

4. The method as claimed in claim 3, wherein the compound is isolated from the aqueous extracts of *Antrodia camphorata*.

5. The method as claimed in claim 3, wherein the compound is isolated from the organic solvent extracts of *Antrodia camphorata*.

6. The method as claimed in claim 5, wherein the organic solvents are selected from the group consisting of alcohols, esters, alkanes, and halogenated alkanes.

7. The method as claimed in claim 6, wherein the alcohol is ethanol.

8. The method as claimed in claim 1, wherein the pancreatic cancer cells are ductal adenocarcinoma cells.

9. The method as claimed in claim 8, wherein the ductal adenocarcinoma cells are from BxPC-3 cell line.

10. The method as claimed in claim 1, wherein the compound is administered in a form selected from the group consisting of powder, tablet, capsule, pellet, granule and liquor.

11. A pharmaceutical composition for inhibiting the survival of pancreatic cancer cells comprising an active dose of compound as claimed in claim 1 and a pharmaceutically acceptable carrier.

12. The composition as claimed in claim 11, wherein the compound is 4--2,3-dimethoxy-6-methyl-5-(3,7,11-trimethyl-dodeca-2,6,10-trienyl)-cyclohex-2-enone.

13. The composition as claimed in claim 12, wherein the compound is isolated from *Antrodia camphorata*.

14. The composition as claimed in claim 13, wherein the compound is isolated from the aqueous extracts of *Antrodia camphorata*.

15. The composition as claimed in claim 13, wherein the compound is isolated from the organic solvent extracts of *Antrodia camphorata*.

16. The composition as claimed in claim 15, wherein the organic solvents are selected from the group consisting of alcohols, esters, alkanes, and halogenated alkanes.

17. The composition as claimed in claim 16, wherein the alcohol is ethanol.

18. The composition as claimed in claim 11, wherein the pancreatic cancer cells are ductal adenocarcinoma cells.

19. The composition as claimed in claim 17, wherein the ductal adenocarcinoma cells are from BxPC-3 cell line.

* * * * *